(12) United States Patent
Milne et al.

(10) Patent No.: US 7,335,170 B2
(45) Date of Patent: *Feb. 26, 2008

(54) THERAPEUTIC MICRO-VIBRATION DEVICE

(76) Inventors: Robert Milne, 2110 Pinto La., Las Vegas, NV (US) 89106; Walter J. Spawr, 2051 Spawr Cir., Lake Havasu City, AZ (US) 86403

( * ) Notice: Subject to any disclaimer, the term of this patent is extended or adjusted under 35 U.S.C. 154(b) by 54 days.

This patent is subject to a terminal disclaimer.

(21) Appl. No.: 11/121,602

(22) Filed: May 4, 2005

(65) Prior Publication Data

US 2006/0253051 A1    Nov. 9, 2006

(51) Int. Cl.
*A61H 1/00* (2006.01)
(52) U.S. Cl. .......................... 601/15; 601/67
(58) Field of Classification Search ............... 601/9, 601/11, 13, 15, 66, 67, 69, 70, 113, 131
See application file for complete search history.

(56) References Cited

U.S. PATENT DOCUMENTS

| | | |
|---|---|---|
| 5,035,235 A | 7/1991 | Chesky |
| 5,103,806 A | 4/1992 | McLeod et al. |
| 5,191,880 A | 3/1993 | McLeod et al. |
| 5,273,028 A | 12/1993 | McLeod et al. |
| 5,304,207 A | 4/1994 | Stromer |
| 5,376,065 A | 12/1994 | McLeod et al. |
| 5,464,436 A | 11/1995 | Smith |
| 5,562,706 A | 10/1996 | Lauterbach et al. |
| 5,632,720 A | 5/1997 | Kleitz |
| 5,645,578 A | 7/1997 | Daffer et al. |
| 5,830,211 A | 11/1998 | Santana et al. |
| 6,001,055 A | 12/1999 | Souder |
| 6,231,497 B1 | 5/2001 | Souder |
| 6,245,006 B1 | 6/2001 | Olson |
| 6,344,021 B1 | 2/2002 | Juster et al. |
| 6,461,377 B1 * | 10/2002 | An ............................ 607/96 |
| 6,602,275 B1 | 8/2003 | Sullivan |
| 6,702,837 B2 | 3/2004 | Gutwein |
| 6,746,473 B2 | 6/2004 | Shanks et al. |
| 2004/0054386 A1 | 3/2004 | Martin et al. |
| 2004/0147984 A1 | 7/2004 | Altshuler et al. |
| 2004/0225339 A1 | 11/2004 | Yaroslavsky et al. |
| 2004/0260210 A1* | 12/2004 | Ella et al. ..................... 601/7 |
| 2004/0260212 A1* | 12/2004 | Cho ............................ 601/15 |
| 2005/0015121 A1 | 1/2005 | Molina |
| 2006/0122631 A1* | 6/2006 | Kertz ......................... 606/131 |

* cited by examiner

*Primary Examiner*—Michael A. Brown
(74) *Attorney, Agent, or Firm*—Armstrong Teasdale LLP; Eric T. Krischke

(57) ABSTRACT

A therapeutic micro-vibration massaging device that also generates both a dynamic induction magnetic force field and an electromagnetic photonic optical light beam field, accompanied by audible acoustic sound, that penetrates the human body, induces an increase in cellular energy and thereby promotes a curative healing effect that reduces or eliminates pain.

39 Claims, 3 Drawing Sheets

DIRECTION OF ROTATION CAN BE CLOCKWISE OR COUNTER-CLOCKWISE

THERAPEUTIC MICRO-VIBRATION DEVICE

FIELD OF THE INVENTION

The embodiments of the present invention relate to a medical therapy device that utilizes micro-vibratory massaging action with magnetic and photonic light beam fields, accompanied by sound waves, to induce an increase in cellular energy thereby providing pain reduction and healing in living cells.

BACKGROUND

The use of vibrating devices for massaging painful areas on the human body by stimulating blood flow has long been considered beneficial. Photonic light beam therapy, typically utilizing laser beams, for relieving pain and healing anomalous tissue has also been used with varying levels of success. Static and pulsating magnetic field therapy has been used for many years throughout the world with varying levels of success. Sound waves, including music, for relieving tension and soothing the human body have also been used. There is, however, no prior art that discloses or suggests coordination and integrative merging of the above-identified technologies in such a manner to bring about a synergistic enhancement of all four technologies.

The prior art discloses the use of electrically driven vibrators and massagers that produce vibration that stimulates circulation to affected tissues. Also, vibration and impact devices are known in the art to encourage bone growth. For example, U.S. Pat. No. 5,273,028 to Kenneth J. McLeod discloses an apparatus for stimulating bone growth in a living organism by transmitting vertical vibrations through a plate upon which the person stands. U.S. Pat. Nos. 5,103,806, 5,376,065 and 5,191,880 also to McLeod, claim methods for preventing osteopenia while promoting growth and healing of bone tissue, including fractured bones, by subjecting the bone to a mechanical load.

U.S. Pat. No. 6,245,006 to Olson describes magnetic therapy as an established and reliable technology. U.S. Pat. No. 5,632,720 to Kleitz describes a motor driven magnetic massage wand which, during use, comes no closer than 18 inches to the human body. Therefore, the wand does not need to come into physical contact with the body. The wand uses a magnetic field between 950 to 1050 gauss in intensity to facilitate an increase in blood flow.

U.S. Pat. No. 6,602,275 to Sullivan discloses the use of dispersed photon light waves at 470 nm, 630 nm and 880 nm to stimulate the human healing process by reducing inflammation, stimulating and rebalancing the electromagnetic energy field surrounding living organisms and detoxifying organs and tissue.

U.S. Pat. No. 5,035,235 to Chesky discloses the use of musical sound waves as therapy for chronic and acute pain. U.S. Pat. No. 5,645,578 to Daffer et al also describes a therapeutic device that utilizes musical tones.

Many of the prior art devices are large and expensive and may require a patient to lie down on the device for several hours. Some of the prior art devices are handheld devices but use only one or two of the subject technologies. For instance, U.S. Pat. Nos. 6,001,055 and 6,231,497 to Souder claim a hand held device with one or more rotating permanent magnets and a vibrating massaging feature. None of the prior art devices utilize or suggest the use of mechanical micro-vibration, photon, sonic, and magnetic technologies in a handheld device which provides pain relief in a short period of time (e.g., seconds) from application.

The prior art is thus characterized by numerous disadvantages which are addressed by the embodiments of the present invention. The embodiments of the present invention minimize, and in some cases eliminate, the above-mentioned disadvantages and shortcomings by utilizing integration of technologies in a convenient handheld device. Clinical trials confirm nearly instant pain relief for patients.

SUMMARY

Accordingly, a first embodiment of the present invention comprises a handheld pain relieving device, incorporating an integrative combination of vibration, photon, magnetic and sonic technologies, that can be conveniently directed or applied to an area of the human body suffering from pain or other affliction.

In a first embodiment, the device comprises a motor that produces micro-vibrations and audible signals and drives one or more permanent magnets or electromagnets and one or more light sources. Importantly, the motor produces a very small electromagnetic field so as not to interfere with the magnetic flux generated by the one or more permanent magnets or electromagnets. An applicator end of the device is placed in contact with, or proximate to, an area of the body suffering from pain or related affliction. During clinical trials, the combination of the magnetic, photon, vibration and sound technologies proved to provide pain relief in very short time periods.

The device is unique in the well-established field of magnetic therapy, wherein stationary, static and/or multiple magnets are used, and photon therapy, wherein light beams are used in the absence of magnetic fields and physical massaging vibrations.

Magnetic therapy has been used for thousands of years around the world. Countries, including China, Japan, Russia, France and England have produced many documents on the subject. Around the world, magnetic therapy is considered a safe approach to healing. In the United States however, magnetic therapy is not generally considered a viable approach to healing. Nonetheless, some medical doctors in the United States have reported the use of static magnets to increase the speed at which bone fractures heal.

One area where magnetic technology has been extensively used in the United States is Magnetic Resonance Imaging (MRI) technology. An MRI device generates a magnetic field, in the order of tens of thousands of gauss, which is directed at a human body for exposing or producing images or pictures of anomalous areas. An MRI is not used as a curative or healing therapy. In contrast, the embodiments of the present invention generate magnetic fields less than ten gauss.

Recently issued U.S. Pat. No. 6,344,021 to Juster et al discloses that magnetic therapy speeds healing by boosting the body's synthesis of adenosine triphosphate (ATP). ATP is considered the fuel that fires all cellular processes and enhances the blood's ability to carry oxygen. Each individual cell possesses a positive electrical charge at its nucleus and a negative charge at its outer membrane. To properly function, the cells and nervous system rely on direct current (DC) and pulsed DC electrical energy. Consequently, life cannot exist without the flow of electricity. The '021 Patent also reveals that static magnetic therapy requires lengthy periods of time (e.g., hours to days) before relief is realized by the patient. The embodiments of the present invention, however, utilize the specific combination of technologies to induce the flow of electricity in afflicted areas. Based on extensive clinical trials, patients have been relieved of chronic pain in seconds to minutes of treatment according to the embodiments of the present invention.

It is well known in the art that vibratory massage provides mechanical stimulation of tissues to increase blood flow to affected areas and enhance pain relief.

Laser light beams are routinely used in medical facilities for the treatment of a broad range of conditions including wound healing, edema reduction and post-operative pain relief. Light beams are directed to small areas or large areas of tissue depending on the condition and specific needs. For example, light beam therapy is routinely used in conventional medical hospital environments on newborn babies afflicted with yellow jaundice. Single lasers, multiple lasers, laser diodes and arrays are used to facilitate light beam therapy. U.S. Pat. No. 6,746,473 to Shanks and Tucek discloses the use of multiple laser diode sources providing a continuous beam and another beam producing a spot of pulsed laser light.

Sound waves have been used for centuries to both relax and stimulate human beings. This is one reason music has been popular since the dawn of mankind. Also, ultrasound technology is well known for therapeutic use to produce thermal and non-thermal effects.

These together with other objects and advantages which will become subsequently apparent from the details of the construction and operation as more fully hereinafter described and claimed.

BRIEF DESCRIPTION OF THE DRAWINGS

The above and other objects, features and advantages of the embodiments of the present invention will become apparent from a consideration of the subsequent detailed description presented in connection with the accompanying drawings in which.

DETAILED DESCRIPTION

Figure 1:
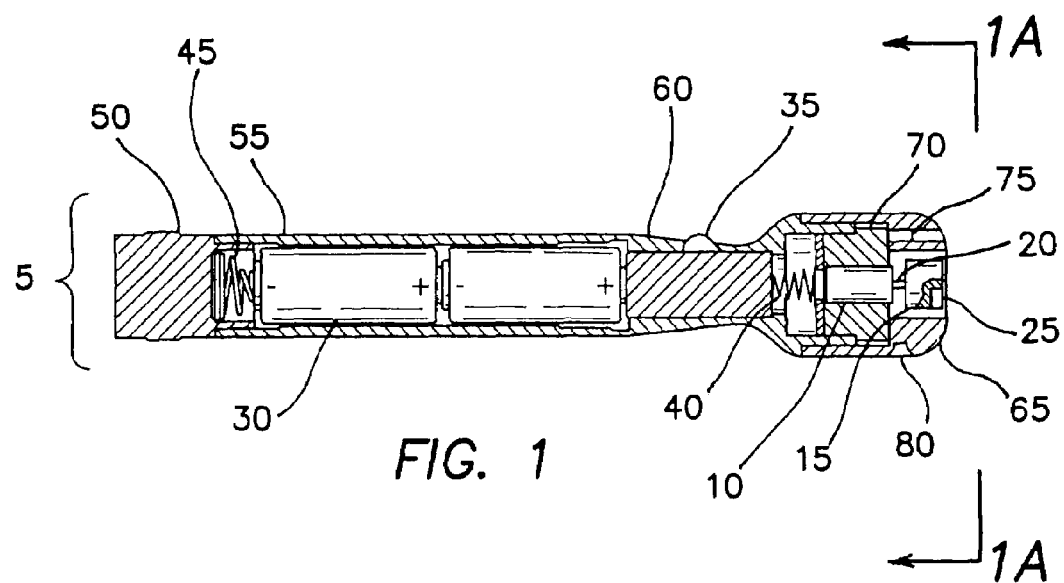
FIG. 1 shows a cross-section view along a length of a micro-vibration device of a first embodiment of the present invention.

For the purposes of promoting an understanding of the principles in accordance with the embodiments of the present invention, reference will now be made to the embodiments illustrated in the drawings and specific language will be used to describe the same. It will nevertheless be understood that no limitation of the scope of the invention is thereby intended. Any alterations and further modifications of the inventive feature illustrated herein, and any additional applications of the principles of the invention as illustrated herein, which would normally occur to one skilled in the relevant art and having possession of this disclosure, are to be considered within the scope of the invention claimed.

Applicants have developed a compact pain relief device and method of use for imparting various forms of energy to a human or animal. The device simultaneously provides multi-dimensional, horizontal, vertical and rotary, micro-vibration to selected areas of the body and therefore biological cells. The term "micro-vibration" as used herein shall refer to a rapid, reciprocating linear motion about an equilibrium position or a rapid symmetrical or asymmetric orbital motion about an axis, as well as any other suitable motion consistent with the known meaning of physical "vibration" in the field of physics. Micro-vibration may also be considered any mechanical, photonic, magnetic and sonic or acoustic vibration which, when the device is placed in contact with tissue, does not cause the tissue to move more than one-half millimeter in any direction.

Figure 2:
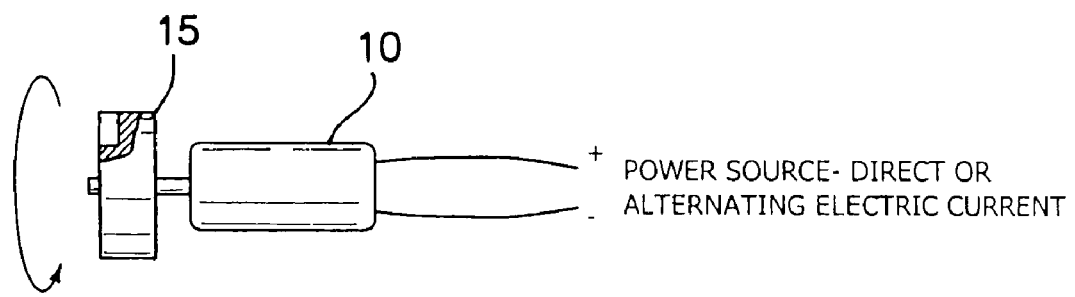
FIG. 2 shows a motor driving a magnet holder of the first embodiment the present invention.
Figure 3:
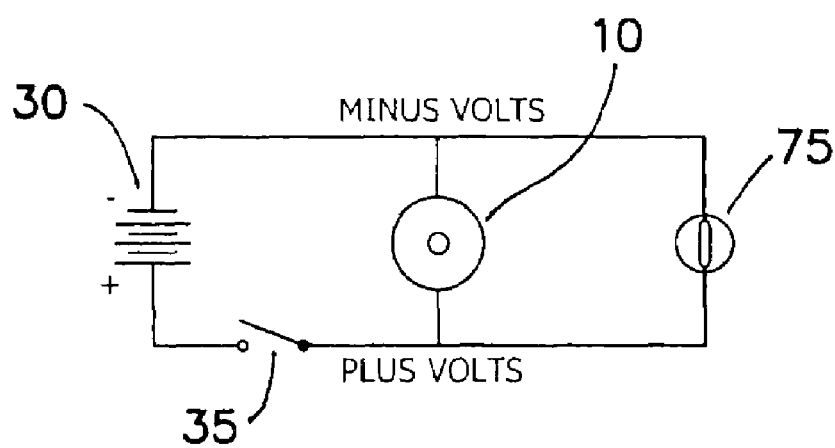
FIG. 3 is a schematic of an electrical circuit used to provide electrical power to micro-vibration device having one light source of the first embodiment of the present invention.

A first embodiment of the present invention is illustrated in FIGS. 1-3. The therapeutic device 5 comprises an electric motor 10 with a magnet holding fixture 15 attached to a motor shaft 20. Permanent magnet or electromagnet 25 is attached and held in place within holding fixture 15. As the permanent magnet or electromagnet 25 is connected to the shaft 20 in an offset manner, permanent magnet or electromagnet 25 is rotatably driven about the centerline of motor shaft 20 by motor 10. Depending on the use, the magnet 25 may be rotated at a constant or alternating rate of 500 to 50,000 revolutions per minute. Ideally, the intensity of the generated magnetic field is less than ten gauss. Importantly, the motor 10 should produce only a very small electromagnetic field so as not to interfere with the magnetic flux generated by the one or more permanent magnets or electromagnets 25. For example, the motor 10 may produce a magnetic or electromagnetic field with an intensity of less than 1% of that generated by the one or more magnets 25.

The motor 10 is powered by batteries 30 in response to electrical switch 35 being turned on. As shown, the positive voltage (+) from batteries 30 flows through electrical conductor 40 to motor 10 and the negative voltage (−) flows through electrical conductor 45, battery holding cap 50, device enclosure 55, switch holding enclosure 60, enclosure embodiment 65 and motor holding fixture 70 to motor 10.

Figure 1A:
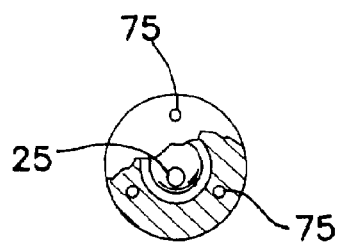
FIG. 1A shows a cross-section along direction A.

Photonic light is produced by one or more light sources 75, such as light bulbs. A laser or a light emitting diode may be used as well. Light sources 75 are electrically energized in a manner similar to motor 10. FIG. 1A shows a cross-section end view which details magnet 25 and multiple light sources 75. The light may fall into a broadband spectrum of light ranging from ultraviolet to infrared with light wavelengths ranging from 350 nanometers to 1100 nanometers and the light sources 75 are directed into the magnetic field produced by magnet 25.

The combined magnetic field created by permanent magnet or electromagnet 25 and the photon electromagnetic field in the optical spectrum should not create any bulk heat in living cells. Accordingly, the photonic electromagnetic field in the optical light spectrum can be either continuously illuminating or pulsating such that the amplitude of the light intensity oscillates up and down in magnitude. In addition, the photonic electromagnetic field in the optical light spectrum may have either one or multiple discrete narrow bands of light of 30 nanometers (nm) or less in width that individually pulsate or change intensity amplitude by oscillating up and down in magnitude or become intermittent within the broadband light spectrum field.

The micro-vibration massage of the first embodiment of the present invention is produced by activating motor 10 to rotate the magnet holding fixture 15. The physical vibration, herein referred to as micro-vibration, is then transferred through motor holding fixture 70 and enclosure 65. The offset attachment of the permanent magnet or electromagnet magnet 25 to the shaft 20 creates oscillating inertial loads which are interpreted by human or animal senses as micro-vibration. When enclosure 65 is placed in contact with human or animal tissue, the micro-vibration is transferred to said tissue. In practice, the magnetic field produced by magnet or electromagnet 25 and the photonic electromagnetic field in the optical spectrum produced by light sources 75 are transferred to, and absorbed by, the body's cells as enclosure 65 is placed in contact with, or proximate to, the body. Running motor 10 and/or solid state sound generator (not shown) also produces an audible sonic sound that is likewise absorbed by the body. A sound transducer or voice coil speaker 80 is electrically driven in a manner similar to motor 10. The voice coil 80 produces a soothing sound that is, as disclosed above, stimulating to human cells.

Figure 2A:
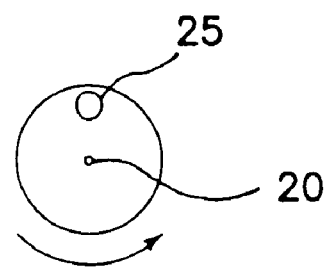
FIG. 2A shows an end view of the magnet holder of FIG. 2.
Figure 3A:
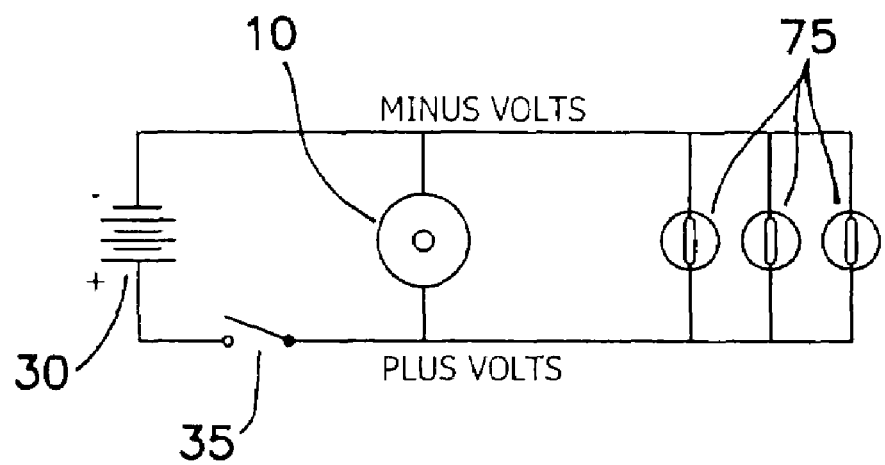
FIG. 3A is a schematic of an electrical circuit used to provide electrical power to micro-vibration device having multiple light sources of the first embodiment of the present invention.

FIGS. 2 and 2A illustrate the relationship between motor 10, magnet holding fixture 15 and magnet 25. Basically, the power source (e.g., batteries 30) drives the motor 10 that in turn rotates the magnet holding fixture 15 and contained magnet 25. FIGS. 3 and 3A illustrates an electrical schematic for the first embodiment of the present invention having one or multiple light sources 75, respectively. The schematic of FIG. 3 comprises a power source 30, motor 10, light source 75 and on-off switch 35. The schematic of FIG. 3A comprises a power source 30, motor 10, multiple light sources 75 and on-off switch 35.

It has been found that a small rotating magnetic field, as generated by a single rotating magnet, produces enhanced electron flow within cells being stimulated by light photons from the light sources 75. The synergistic effect increases the elimination of pain 5-10 times faster than photonic stimulation alone.

Although the invention has been described in detail with reference to several embodiments, additional variations and modifications exist within the scope and spirit of the invention as described and defined in the following claims.

We claim:

1. A hand held therapeutic device for relieving pain and providing a curative healing effect comprising:
   one or more permanent magnets or electromagnets attached to an end of a shaft in an offset manner such that the permanent magnets or electromagnets may rotate in a circular pattern defined by a radius from a centerline of said shaft wherein with multiple permanent magnets or electromagnets said multiple permanent magnets or electromagnets are spaced unevenly about a circle of rotation;
   a motor for rotatably driving said one or more offset permanent magnets or electromagnets to generate a dynamic magnetic field, which penetrates living tissue, and micro-vibrations in the form of oscillating inertial loads resulting from the rotation of the one or more offset permanent magnets or electromagnets about the centerline of the shaft;
   one or more light sources for generating a photonic light field in an optical light spectrum; and
   means for producing audible acoustic tones.

2. The device according to claim 1 wherein said one or more light sources produce a photonic light field in a broadband spectrum of light ranging from ultraviolet to infrared.

3. The device of claim 2 wherein light wavelengths range from 350 nanometers to 1100 nanometers.

4. The device according to claim 1 wherein, upon contact with said device, a compliant body or surface does not move more than one-half millimeter in distance in any direction.

5. The device according to claim 1 wherein said magnetic field and said photonic light field do not produce bulk heating in living cells or tissue.

6. The device of claim 1 wherein said magnetic field is no more than ten gauss of field intensity.

7. The device according to claim 1 wherein said magnetic field is created by rotating said permanent magnet at an alternating or constant rate between 500 and 50,000 revolutions per minute.

8. The device according to claim 1 wherein said photonic light field in the optical light spectrum can be either continuously illuminating or pulsating such that the amplitude of the light intensity oscillates up and down.

9. The device according to claim 1 wherein said photonic light field in the optical light spectrum may have either one or multiple discrete narrow bands of light having a width of 30 nanometers or less that individually pulsate or change intensity amplitude by oscillating up and down or become intermittent within a broadband light spectrum field.

10. The device according to claim 1 wherein said audible acoustic tones are relaxing and soothing to human senses.

11. The device according to claim 1 wherein said device produces microvibratory, electromagnetic, photon, biochemical stimulation that induces a change in cellular energy.

12. The device according to claim 1 wherein said magnetic field alters cellular energy in living organisms.

13. The device according to claim 1 wherein the combination of magnetic, photon, vibration and sonic sound wave technologies results in a reduction in pain in less than five minutes.

14. The device according to claim 1 wherein at least one of said motor and a speaker produces audible acoustic tones.

15. The device of claim 1 wherein the motor produces a magnetic or electromagnetic field which does not interfere with said dynamic magnetic field generated by the rotation of said one or more permanent magnets or electromagnets.

16. The device of claim 1 wherein the motor does not produce a magnetic or electromagnetic field greater than one percent of a dynamic magnetic field generated by the rotation of the one or more permanent magnets or electromagnets.

17. A hand held therapeutic device for relieving pain and providing a curative healing effect comprising:
   a motor for rotating one or more permanent magnets or electromagnets to generate a magnetic field, micro-vibrations and audible acoustic tones;
   a shaft connecting said one or more permanent magnets or electromagnets to said motor, said one or more permanent magnets or electromagnets connected to said shaft in an offset configuration such that said one or more permanent magnets or electromagnets may rotate in a circular pattern defined by a radius from a centerline of the shaft wherein with multiple permanent magnets or electromagnets said permanent magnets or electromagnets are spaced unevenly about a circle of rotation thereby generating micro-vibrations in the form of oscillating inertial loads; and
   one or more light sources for generating a photonic light field in the optical light spectrum.

18. The device of claim 17 wherein said magnetic field comprises a moving magnetic field pattern with a centerline of said magnetic field running parallel to a centerline of the rotating shaft.

19. The device according to claim 17 wherein said one or more light sources produce a photonic light field in a broadband spectrum of light ranging from ultraviolet to infrared.

20. The device of claim 19 wherein light wavelengths range from 350 nanometers to 1100 nanometers.

21. The device according to claim 17 wherein said motor generates micro-vibrations such that, upon contact with said device, a compliant body or surface does not move more than one-half millimeter in distance in any direction.

22. The device according to claim 17 wherein said magnetic field and photonic light field do not produce bulk heating in living cells or tissue.

23. The device of claim 17 wherein said magnetic field is no more than ten gauss.

24. The device according to claim 17 wherein said magnetic field is created by rotating said one or more permanent magnets or electromagnets at an alternating or constant rate between 500 and 50,000 revolutions per minute.

25. The device according to claim 17 wherein said photonic light field in the optical light spectrum can be either continuously illuminating or pulsating such that the amplitude of the light intensity oscillates up and down in magnitude.

26. The device according to claim 17 wherein said photonic light field in the optical light spectrum may have either one or multiple discrete narrow bands of light of 30 nanometers or less in width that individually pulsate or change intensity amplitude by oscillating up and down or become intermittent within a broadband light spectrum field.

27. The device according to claim 17 wherein said device produces vibratory, magnetic, photon biochemical stimulation that induces a change in cellular energy.

28. The device according to claim 17 wherein said magnetic field alters cellular energy in living organisms.

29. The device of claim 17 wherein the specific integration of micro-vibration, magnetic, photon, audible and/or acoustic sound wave technologies produces a reduction in pain in less than five minutes.

30. The device of claim 17 wherein the motor produces a magnetic or electromagnetic field that does not interfere with said magnetic field generated by said magnets.

31. The device according to claim 17 wherein the motor does not produce a magnetic or electromagnetic field greater than 1% of the dynamic magnetic field generated by the one or more rotating magnet.

32. A method of administering pain relief with a hand-held device comprising:

rotating one or more permanent magnets or electromagnets to generate a magnetic field, said magnetic field comprising moving circular magnetic field pattern with a centerline of the magnetic field running parallel to a centerline of a rotating shaft attaching said one or more permanent magnets or electromagnets to a motor;

generating a photonic light field in an optical light spectrum wherein said light field is directed into the magnetic field;

generating micro-vibrations by rotating said one or more permanent magnets electromagnets, attached to an end of a shaft in an offset manner, in a circular pattern defined by a radius from a centerline of said shaft wherein with multiple permanent magnets or electromagnets said multiple permanent magnets or electromagnets are spaced unevenly about a circle of rotation;

generating audible acoustic tones; and placing the hand-held device in contact with, or proximate to, a pain area on a human or animal body.

33. The method of claim 32 further comprising producing light wavelengths ranging from 350 nanometers to 1100 nanometers.

34. The method according to claim 32 further comprising generating micro-vibrations such that, upon contact with said device, a compliant body or surface does not move more than one-half millimeter in distance in any direction.

35. The method according to claim 32 further comprising producing said magnetic field and photonic optical light field and micro-vibrations such that no bulk heating is formed in living cells or tissue.

36. The method according to claim 32 further comprising generating said magnetic field by rotating said permanent magnet at an alternating or constant rate between 500 and 50,000 revolutions per minute.

37. The method according to claim 32 further comprising producing said photonic light field in the optical light spectrum having either one or multiple discrete narrow bands of light of 30 nanometers or less in width that individually pulsate or change intensity amplitude by oscillating up and down in magnitude or become intermittent within the broadband light spectrum field.

38. The device according to claim 32 wherein generating micro-vibrations and audible acoustic tones is accomplished with the motor and/or speaker.

39. The device according to claim 32 wherein the motor does not produce a magnetic or electromagnetic field greater than 1% of a dynamic magnetic field generated by the one or more rotating permanent magnets or electromagnets.

* * * * *